(12) United States Patent
Jones

(10) Patent No.: US 7,967,965 B2
(45) Date of Patent: *Jun. 28, 2011

(54) GAS SENSOR

(75) Inventor: Martin Jones, Havant (GB)

(73) Assignee: Honeywell International Inc., Morristown, NJ (US)

( * ) Notice: Subject to any disclaimer, the term of this patent is extended or adjusted under 35 U.S.C. 154(b) by 480 days.

This patent is subject to a terminal disclaimer.

(21) Appl. No.: 11/747,632

(22) Filed: May 11, 2007

(65) Prior Publication Data

US 2008/0277290 A1    Nov. 13, 2008

(51) Int. Cl.
*G01N 27/407* (2006.01)
(52) U.S. Cl. ........ 204/431; 204/400; 204/412; 204/430; 205/775; 205/782; 205/788; 502/182
(58) Field of Classification Search ................... 204/400, 204/412, 413, 430, 431; 205/775, 782, 788; 502/182
See application file for complete search history.

(56) References Cited

U.S. PATENT DOCUMENTS

| | | | |
|---|---|---|---|
| 4,406,770 A | | 9/1983 | Chan et al. |
| 4,407,905 A | | 10/1983 | Takeuchi et al. |
| 4,824,549 A | * | 4/1989 | Hamada et al. ............... 204/410 |
| 5,429,727 A | * | 7/1995 | Vogt et al. .................. 205/779.5 |
| 5,650,054 A | * | 7/1997 | Shen et al. .................... 204/412 |

FOREIGN PATENT DOCUMENTS

| | | |
|---|---|---|
| EP | 0 298 570 | 1/1989 |
| GB | 1443 354 | 7/1976 |
| WO | WO 2005/015195 | 2/2005 |

OTHER PUBLICATIONS

Hobbs, B.S., et al., Liquid Electrolyte Fuel Cells, Techniques and Mechanisms in Gas Sensing, 1991, pp. 161-188, IOP Publishing, Bristol, England.
Smith, A.D., Use of Exhaled Nitric Oxide Measurements to Guide Treatment in Chronic Asthma, N Engl J Med 2005; 352:2163-2173.
Ashutosh, Kumar, M.D., Nitric Oxide and Asthma: a review, Current Opinion in Pulmonary Medicine 2000, 6:21-25.
Ricciardolo, Fabio L.M., Nitric Oxide in Health and Disease of the Respiratory System, Physiol Rev 2004; 84:731-765.
EP Search Report for application 08251664.2 dated Oct. 19, 2009 (6 pages) for companion EP case.

* cited by examiner

*Primary Examiner* — Nam X Nguyen
*Assistant Examiner* — Susan Thai
(74) *Attorney, Agent, or Firm* — Husch Blackwell

(57) ABSTRACT

The present invention provides a unique solution to the problems of both steady-state and transient signals produced by a variety of interfering stimuli, including humidity, which relies upon the inclusion in a gas sensing electrode in an electrochemical gas sensor of a catalyst material in addition to a first catalyst material reactive to the target gas, the additional, or second, catalyst material producing a response to an interfering stimulus which is of the opposite polarity to that generated by the first catalyst material.

28 Claims, 5 Drawing Sheets

GAS SENSOR

FIELD OF THE INVENTION

The present invention relates to electrochemical gas sensors having reduced sensitivity to interfering stimuli, in particular humidity.

BACKGROUND TO THE INVENTION

Electrochemical gas sensors operate on fuel cell principles, in that the gas or vapour to be sensed is caused to react at an electrode of an electrochemical cell, thereby generating a current which is a function of the concentration of the gas or vapour to be sensed.

Electrochemical gas sensors are widely used for the detection of toxic gases in a variety of applications. These include measurements in industrial environments for personal protection; combustion emission monitoring from fixed and mobile sources to minimise environmental impact and maximise fuel efficiency; monitoring discharges from fixed plant for regulatory certification; and medical applications. Electrochemical gas sensors based on liquid electrolytes and gas diffusion electrodes, typically employing gas diffusion barriers, have been very successful in addressing these and other applications, as described by B. S. Hobbs et al, "Techniques And Mechanisms In Gas Sensing", Chapter 6, 1991, Edited by P. T. Moseley et al. These sensors generally provide a robust, accurate, low cost solution to the demands of instrument manufacturers and end users.

However, there is continuing demand for improved levels of performance to enable more accurate and reliable measurements without a significant increase in the cost or complexity of the technology. Improvements can also allow new applications to be addressed where conventional methods are deemed unacceptable. Such demands typically centre on (i) the specificity of the sensor output to the defined measurand of interest; (ii) higher sensitivity to the gas of interest allowing reliable resolution of concentrations well below statutory limits; and (iii) the ability of the sensor to operate to its specified performance across a wide range of environmental conditions (eg. temperature, humidity). The present invention is particularly concerned with reductions in the humidity cross-interference response of such devices, although the principles employed may be used to enhance other aspects of the behaviour.

The humidity of the sensed environment can affect the performance of an electrochemical gas sensor in two main ways. Over the long term, high or low humidity (particularly if combined with extremes of temperature) can significantly alter the properties of the aqueous electrolyte by exchange of water occurring through the gas access to the sensor. If the electrolyte loses water, its pH rises or falls, depending on whether an alkali or acid system is employed. This may result in damage to sensor components and places more strain on the seals retaining electrolyte within the housing. There is also a significant risk of the sensor drying out, resulting in a loss of electrolytic contact between the electrodes and hence a malfunction. If the electrolyte takes on water it becomes more neutral, which may compromise the activity of the system towards the reactions of interest. In extreme cases, leakage of electrolyte due to pressure build-up may occur. The mechanisms governing these behaviours are generally understood, and sensor designers have evolved a number of strategies to address the problems which arise.

In the short term, relatively rapid, or transient, changes in ambient conditions (typically on a timescale of a few seconds) may affect the instantaneous output of the sensor rather than its long term performance. Such changes may occur in industrial applications when using portable gas detection equipment. For example, it is common for such devices to be carried between adjacent areas of plant experiencing differing conditions. In severe cases, reading errors may temporarily produce a fail-to-danger condition by offsetting the true response to a target measurand (although this is usually very short-lived). A more common problem is that the instrument is put into an alarm condition by the very rapid change in output it experiences. False alarms are very undesirable since they may lead to unwarranted interruptions in operation of the plant and cause a loss of confidence in the instrument.

The mechanisms governing such transient effects are not well understood, but are believed to relate to changes occurring at the 3-phase interface between the gas, liquid electrolyte and solid catalyst which governs the behaviour of these electrochemical systems. The severity of such effects is more marked in some electrochemical systems than others and can be particularly troublesome in sensors with inherently low sensitivity, since in such cases a comparatively small shift in output current is interpreted as a relatively high gas concentration. For example, sensors for ppm-level detection of chlorine and hydrogen chloride employing graphite catalysts are particularly prone to humidity transient problems.

Another situation in which rapid humidity changes are inevitably encountered is in the real-time analysis of exhaled breath. Electrochemical sensors have been used in medical applications such as smoking cessation for many years. However, successful applications have usually involved the measurement of relatively high concentrations (ppm levels or above) of comparatively straightforward measurands such as CO, where high activity can be achieved by conventional sensor designs. Other potential applications are more challenging. One of these is the use of nitric oxide (NO) concentrations as an indicator of pulmonary function and a means of early identification of asthma or other related problems. See, for example, A. D. Smith et al, N. Engl. J. Med. (2005); 352:2163-73; K. Ashutosh, Curr. Opin. Pulm. Med. (2000); 6:21-5; and F. L. Ricciardolo et al, Physiol. Rev. (2004); 84:731-65.

Electrochemical gas sensors utilising conventional graphite electrocatalysts as the basis of their sensing electrodes are capable of detecting NO at the medically relevant concentrations of 0-200 ppb under favourable, controlled conditions. However, they can also exhibit transient signals of several ppm NO equivalent in response to a 0-100% step change in relative humidity (RH). This represents a severe difficulty when the typical level of NO in exhaled breath for a healthy subject is ~15 ppb, but is present in a background whose humidity content can reach 100% RH and varies rapidly with time. A further concern is the additional presence in exhaled breath of other potential cross-interferents, such as $CO_2$ (~5%), $NH_3$, $H_2$, $CH_4$, ketones, ethanol etc., at variable trace levels.

Historically, such gas sensors have been used in industrial safety applications where humidity effects, whilst undesirable, did not necessarily represent a critical problem, bearing in mind the 8-hour exposure limit of 25 ppm NO. However, new evidence has significantly increased concern about the toxicity of NO and the latest recommendation is that exposure levels should be kept below 1 ppm. Therefore, the requirement to address the problem of humidity cross-interference whether in the form of a steady-state (ie. long term) interference or a transient interference is driven not only by the desire to address new applications, but also by the need to respond to more stringent demands from existing users.

One potential method for solving this problem might be to control the RH of the sample entering the sensor. Sample treatment to remove or stabilise humidity levels is well known in large fixed gas detection installations (eg. via cold finger traps or drying filters), albeit at the expense of the rapid response times which are generally required in portable or real-time analysis applications. However, there is currently no viable, low cost, maintenance-free way of achieving the same result in personal monitors.

Another potential approach might be to measure the ambient humidity with a separate sensor and apply an appropriate correction factor. However, experience shows that the magnitude of the humidity transient varies significantly between sensors having a nominally identical construction and is critically dependent upon the rate of change of RH. It is also likely that the effects vary significantly with sensor age. Thus, a simple solution applicable across a wide range of devices throughout their operating life is unlikely to be achieved in this way.

Yet another potential approach might be to mitigate the RH effect at source, ie. by designing an electrochemical reaction scheme which has no humidity response. However, most gases show high activity on comparatively few catalysts, and so the practical options are quite limited. This often means that a compromise must be made in respect of other undesirable effects, such as cross-sensitivity. Traditionally, the intention has been that the response to the primary, or target, measurand be enhanced whilst leaving the response interferent unaffected, or the reactivity to the interferent reduced with a lesser effect upon the primary or target's sensitivity. Ideally, one seeks to achieve both simultaneously to produce optimum performance.

Methods to offset the impact of cross-interferences, in the form of chemical (gas) contaminants, in electrochemical gas sensors are described in U.S. Pat. No. 4,587,003 and WO-A-2005015195. These approaches rely on either (a) the transmission of unreacted gas through the sensing electrode to a second, compensating electrode; or (b) the provision of parallel gas paths to different electrodes. The signals obtained from the two electrodes are then processed to identify and remove the degree of cross-interference observed. Whilst both methods work adequately for steady-state interferences, they are relatively complex to implement, requiring additional components and changes to the usual sensor hardware. They also tend to be less effective in cases where transient behaviour is involved, due to the difficulty in matching the speed of response of the two electrodes.

Another approach has been to alloy the solid catalyst from which the sensing electrode is made with another metal which reduces the sensitivity of the sensing electrode to the cross-interferent. One example has been the use of a platinum/ruthenium alloy in a sensor for sensing $H_2S$, the ruthenium acting to depress the sensitivity of the platinum to contaminant CO. An alternative is a gold/ruthenium alloy in a sensor for sensing $SO_2$, the ruthenium acting to depress the sensitivity of the gold to contaminant CO.

Chemical filters may also be used to improve the selectivity of sensors, a common example being the use of carbon cloth to remove $H_2S$ and alcohols from a CO sensor.

Bias voltage may also be used to remove sensitivity of a sensor to cross-interferences.

SUMMARY OF THE INVENTION

The present invention provides a unique solution to the problems of both steady-state and transient signals produced by a variety of interfering stimuli, including humidity, which relies upon the inclusion in a gas sensing electrode in an electrochemical gas sensor of a catalyst material, in addition to a first catalyst material reactive to the target gas, the additional, or second, catalyst material producing a response to an interfering stimulus which is of the opposite polarity to that generated by the first catalyst material.

In the context of the present Application by "opposite polarity" we mean that the second catalyst material generates in response to the interfering stimulus a current at the gas sensing electrode which is opposite in polarity to the current generated by the first catalyst material in response to the same interfering stimulus. The current generated by response of the first catalyst material to the interfering stimulus may be of the same polarity as or of opposite polarity to, the current generated by that catalyst material on reaction with the target gas. Thus, the electrochemical sensor of the present invention may correct an over-reading or an under-reading of the target gas concentration as a result of the presence of an interfering stimulus.

It is essential that the nature of the second catalyst material and/or the conditions in which it is used (including sensor design) should not unduly compromise the core sensitivity of the sensor to the target gas. In the context of the present Application this means, in the very least, that the sensitivity of the sensor to the target gas in the presence of the second catalyst material should not be worse than that experienced in the presence of the interfering stimulus but without the additional catalyst material. Indeed, preferably, the second catalyst material should enhance the sensivity of the first catalyst material to the target gas, either by interaction with the first catalyst material or the second catalyst material should itself have a positive response to the presence of the target gas. Furthermore, the second catalyst material should desirably not introduce cross-sensivities to other species. Ultimately, however, this will depend upon the environment in which the sensor is to be used, and in particular whether such cross-sensitivities are present.

There are a number of ways in which the second catalyst material may be deployed within an electrochemical gas sensor in order to achieve the above-described effects. For instance, the second catalyst material may be mixed, or otherwise arranged, with the first catalyst material in a single gas sensing electrode. Alternatively, the second catalyst material may be present in a different gas sensing electrode to the first catalyst material.

According to a first aspect of the present invention, therefore, an electrochemical gas sensor for sensing a target gas comprises a gas sensing electrode; a counter electrode; and an electrolyte with which both the gas sensing electrode and the counter electrode are in contact, wherein the gas sensing electrode comprises a first catalyst material reactive to the target gas and which produces a response to an interfering stimulus, and a second catalyst material which produces a response to the interfering stimulus of opposite polarity to the response of the first catalyst material to that interfering stimulus.

According to a second aspect of the present invention an electrode comprises, supported on or dispersed within a support material, a catalyst composition comprising a first catalyst material reactive to the target gas and which produces a response to an interfering stimulus, and a second catalyst material which produces a response to the interfering stimulus of opposite polarity to the response of the first catalyst material to the same interfering stimulus.

According to a third aspect of the present invention, an electrochemical sensor for sensing a target gas and generating a sensor output related to the concentration of the target gas, comprises a first gas sensing electrode comprising a first catalyst material reactive to the target gas and which produces a response to an interfering stimulus; a second gas sensing electrode comprising a second catalyst material which produces a response to the interfering stimulus of opposite polarity to the response of the first catalyst material to that interfering stimulus; a counter electrode; an electrolyte with which each of the gas sensing electrodes and the counter electrode are in contact; and means for electronically processing the responses of the first and second gas sensing electrodes to the interfering stimulus, so as to reduce or cancel out the effect on sensor output of the interfering stimulus.

By adjustment of the relative proportions of the first and second catalyst materials, it is possible to reduce or completely cancel out the effect of an interfering stimulus, whether transient or steady-state, and thereby produce a simple robust solution to the above-described problem.

Further aspects of the present invention are defined in the claims, including a catalyst composition and a coating composition comprising said catalyst composition, for preparing an electrode according to the second aspect of the present invention.

DETAILED DESCRIPTION OF THE INVENTION

The electrochemical gas sensor of the present invention may be designed to reduce or eliminate the interfering effect of a wide variety of interfering stimuli. In this context, an "interfering stimulus" refers to a condition or species within the environment of the sensor which causes a current to be generated at the gas sensing electrode, other than the target gas species which the gas sensing electrode is designed to detect. By way of example, the term includes chemical interferents, for instance any gas species other than the target gas species which reacts significantly on the gas sensing electrode to generate a potential therein; or an environmental interferent, for instance humidity. As is clear from the above, of primary interest is the effect of relative humidity, and in particular transient effects of humidity. As a consequence, in what follows the present invention will be described primarily in terms of reducing or cancelling out transient humidity effects in electrochemical gas sensors. However, the present invention should not be considered limited to this, preferred, embodiment, but should be construed so as to apply also to other transient effects, and to steady-state effects.

The nature of the first and second catalyst materials depends upon the nature of the target gas and the interfering stimulus, respectively. What is key is that the second catalyst material has a response to the interfering stimulus which is of opposite polarity to the response of the first catalyst material to the same interfering stimulus. Different applications will tolerate different degrees of cancellation of the response to the interfering stimulus. Generally, however, it is preferred that the response generated by the second catalyst is opposite in polarity and substantially equal in magnitude to that of the first catalyst material.

The response to the interfering stimulus generated by the second catalyst material may be adjusted in magnitude in a number of different ways, including choice of appropriate concentration and/or surface area of the first and/or second catalyst materials, or by other aspects of sensor design, such as by electronic manipulation, and/or by arranging for a different volume of the target gas to reach the second catalyst material.

The present invention is now described in terms of the first aspect but the same considerations in terms of types of first and second catalyst materials and sensor design, also apply to the third aspect of the present invention, in which separate gas sensing electrodes are used to reduce or cancel out the effect of an interfering stimulus.

The gas sensing electrode may be any of the conventional types, adapted so as to include a first catalyst material and a second catalyst material, as defined above. Indeed, another advantage with the present invention is that the change in catalyst formulation lends itself to existing electrode manufacturing routes, and there is no requirement for hardware changes to the remainder of the sensor.

For instance, the gas sensing electrode may comprise a catalyst composition comprising the first and second catalyst materials coated on or dispersed within a suitable support material. The catalyst composition may be mixed with conventional solvents, surfactants and/or binders for this purpose to produce a printable ink, puddling slurry, or spray solution, which may then be coated on to or sprayed onto a support material to form the gas sensing electrode. The choice of catalyst deposition route may affect the overall performance of the device, but is not critical to the operation of the humidity cancellation mechanism.

In the case of a gas diffusion electrode, optimum for portable gas sensors, the support material will preferably be a gas-permeable hydrophobic tape, for instance of polytetrafluoroethylene (PTFE) or some other fluorocarbon polymer, in order to allow good accessibility to both the target gas and the electrolyte. Another option is to form the gas sensing electrode by mixing a catalyst composition comprising the first and second catalyst materials with a powdered hydrophobic material, for instance PTFE, and a binder, and then compressing the resultant mixture into tablet form or other solid form. Other options are generally known in the field.

In the case of other types of gas sensing electrode, electrode design and materials are selected in accordance with what is generally known in the field. For instance, the electrode may be a suitably constructed metal foil or mesh.

The present invention will now be described with reference to the accompanying drawings, in which.

Figure 4:
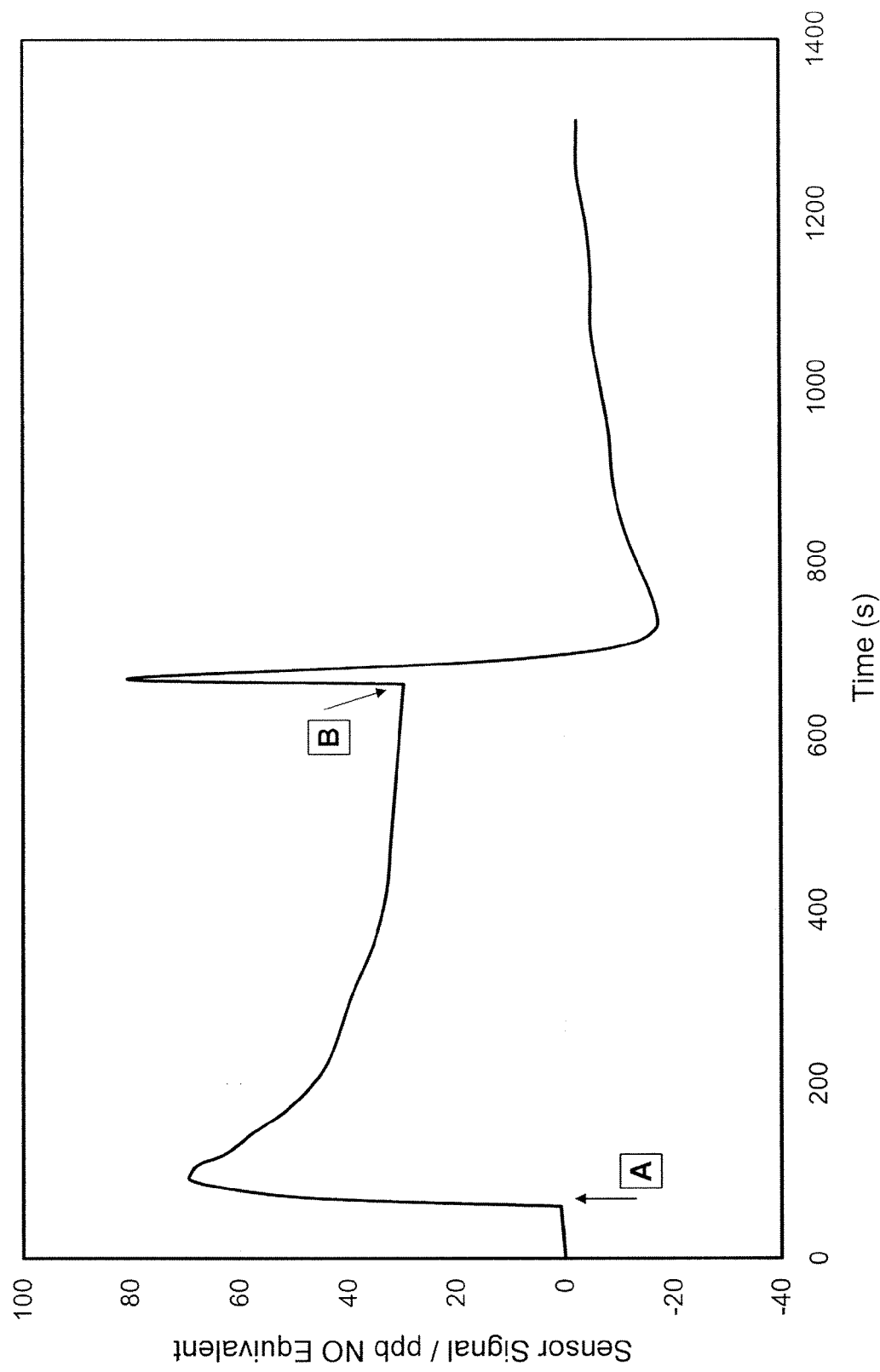
Figure 5:
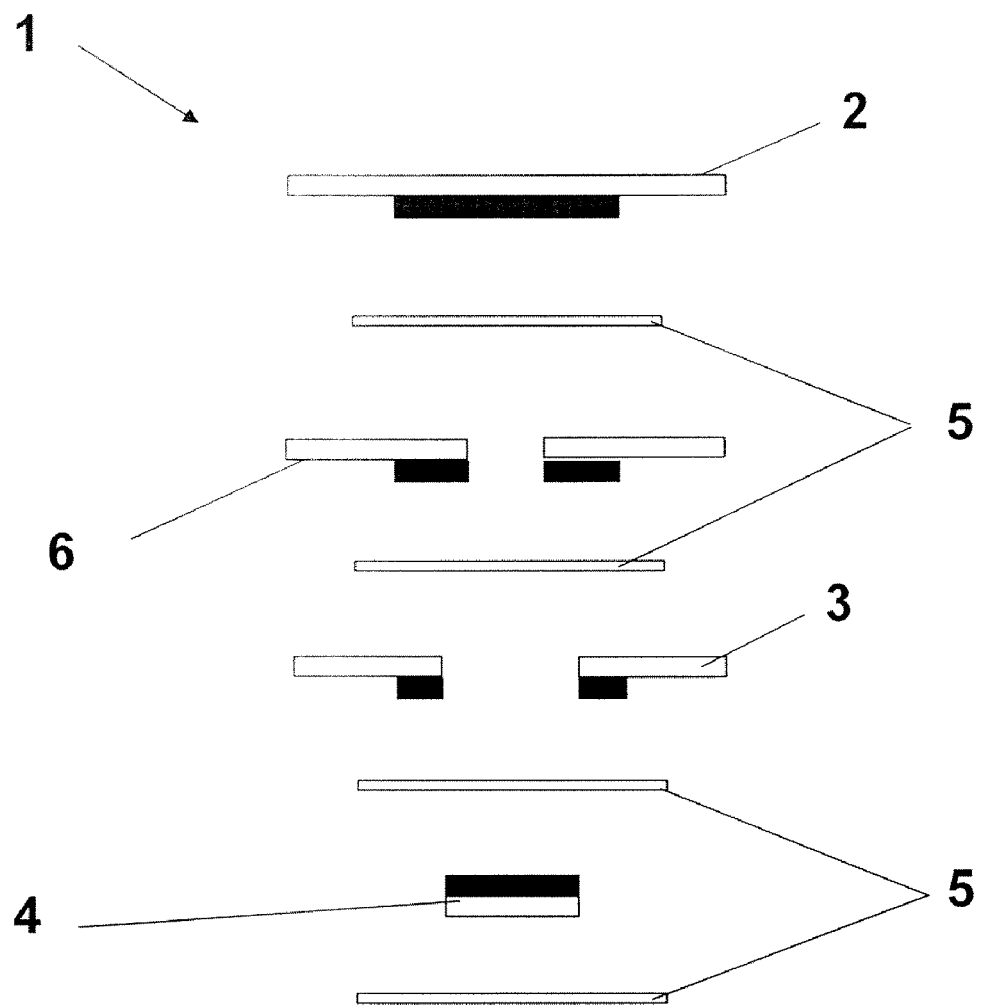

FIG. 4 shows humidity transient in the baseline response of an open electrode NO sensor with a mixed 3 weight % ruthenium black/graphite sensing electrode when subjected to a relative humidity cycle of between 0% and 100%; and FIG. 5 shows a schematic cross-section of an electrode stack assembly of a low level NO electrochemical gas sensor of the type used in the present invention.

Figure 1:
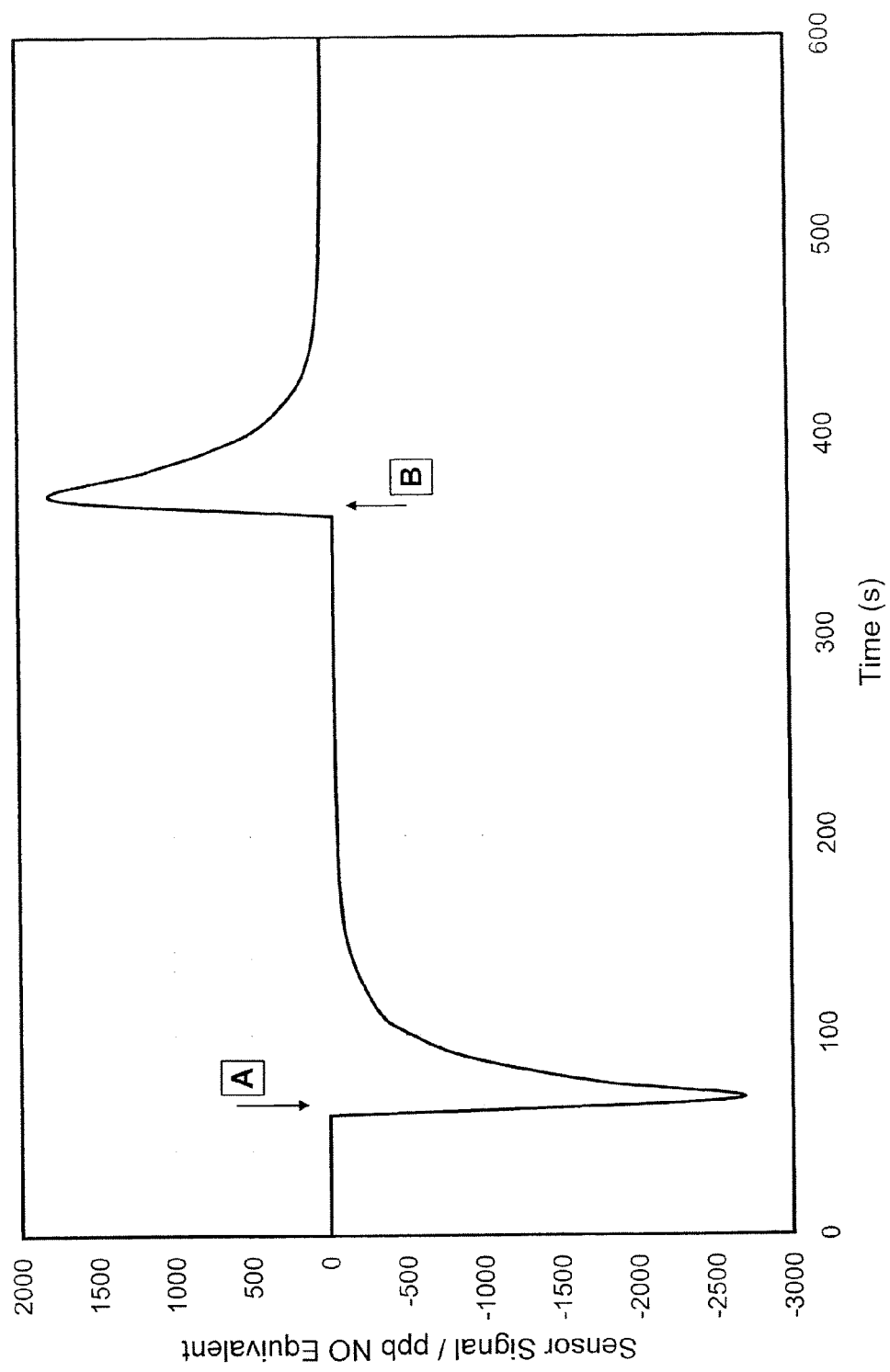
FIG. 1 is a graph showing humidity transients in the baseline response (ie. in the absence of target gas) of an open electrode NO sensor with a conventional low surface area graphite sensing electrode when subjected to a relative humidity cycle of between 0% and 100%.

A conventional electrochemical NO sensor typically used for safety monitoring applications (eg. 7NT manufactured by City Technology Ltd, Portsmouth, UK) employs a graphite sensing electrode catalyst. FIG. 1 shows the behaviour to humidity of an open electrode sensor of this type, ie. one which has not been fitted with a capillary barrier. Open electrode sensors are often used when optimising catalyst properties since they allow the true full activity of the materials to be determined. To a first approximation, this simply means that the magnitudes of both the target gas sensitivity and interfering effects due to humidity are increased pro rate over their values in a capillary controlled device. In more detail, the gas sensing electrode was of low surface area graphite (of the type used in the Example below) printed onto a porous PTFE backing type, and the reference and counter electrodes were each of platinum black printed onto porous PTFE backing types. The electrolyte was 5M $H_2SO_4$ and the bias voltage +300 mV (ie. the gas sensing electrode is biased at 300 mV with respect to the reference electrode).

In FIG. 1 "A" denotes a dry-to-wet step change in humidity, and "B" denotes a wet-to-dry change in humidity. Throughout the following description, 'dry' and 'wet' are used to refer to nominal 0%, and 100% relative humidities (RH) at an ambient temperature of approximately 20° C. As can be seen, the sensor output registered a negative concentration of NO in response to an upward step in RH and vice versa. This behaviour has been defined as a "negative humidity transient".

For this general type of NO sensor (ie. one having a graphite sensing electrode), the second catalyst material may be any metal which exhibits a positive response to relative humidity, to counter the negative response exhibited by the graphite, and which would otherwise result in the gas sensing electrode apparently measuring a lower concentration of NO than actually present in the environment of interest. The second catalyst material is typically selected from the transition metals, preferably those which are relatively unreactive, or "noble". The preferred second catalyst material for this application is ruthenium metal or a compound thereof, for instance ruthenium oxide ($RuO_2$).

Figure 2:
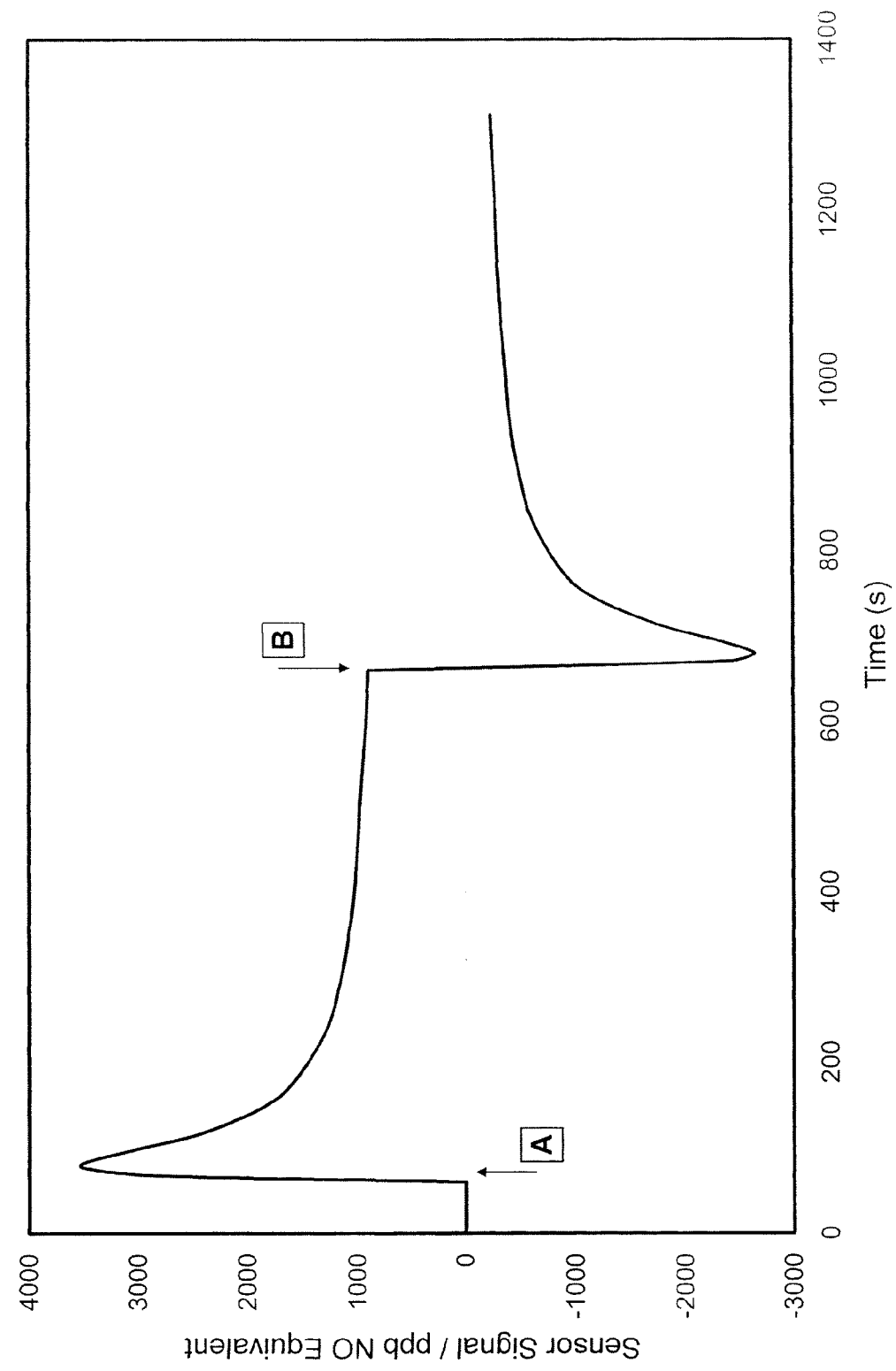
FIG. 2 is a graph showing humidity transients in the baseline response of an open electrode NO sensor with a ruthenium black sensing electrode when subjected to a relative humidity cycle of between 0% and 100%.

When built into an open electrode sensor of the same type used to generate FIG. 1, a gas sensing electrode of comparable construction but employing a ruthenium black catalyst (rather than graphite) gave a response to the same humidity conditions of the opposite polarity, as illustrated in FIG. 2. As in FIG. 1, "A" denotes a dry-to-wet step change in humidity, and "B" denotes a wet-to-dry change in humidity. The "positive humidity transient" observed (ie. increasing NO equivalent output in response to a step increase in RH and vice versa) is the key property required to allow reduction or cancellation of the humidity effect observed on graphite, and illustrated in FIG. 1.

Figure 3:
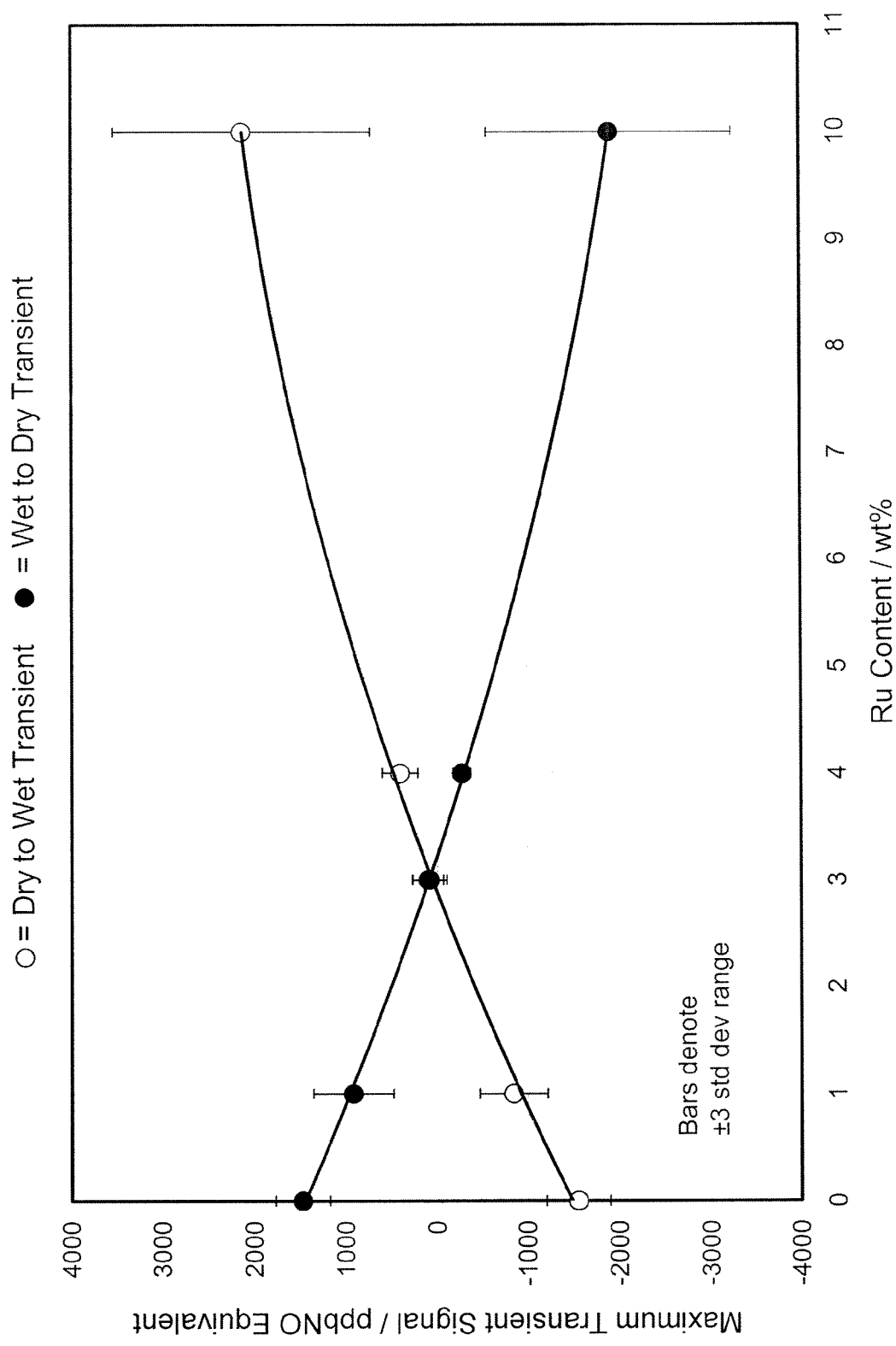
FIG. 3 shows the variation in the maximum humidity transient signals observed for open electrode NO sensors with ruthenium loading in the graphite sensing electrode.

FIG. 3 again shows open electrode data for low surface area graphite sensing electrodes in response to NO. But here, the effect of differing levels of ruthenium black upon the peak magnitude of the rising and falling humidity transient is also shown. This clearly indicates that the polarity and magnitude of the resultant humidity transient is critically dependent upon the ruthenium content of the catalyst As FIG. 3 shows, some reduction in the response to RH was achieved with an amount of ruthenium of greater than 0 weight % up to about 7 weight %, based on the total weight of graphite and ruthenium. Indeed, some reduction may be achieved with higher amounts of ruthenium. The greatest reduction in the RH transient was observed at a ruthenium loading of about 2 weight % to about 4 weight %. At a 3 weight % loading of ruthenium the overall response to RH was virtually eliminated, resulting in no significant transients for changes in humidity from both dry to wet and wet to dry conditions.

A typical open electrode plot using an electrode with the composition 97 weight % graphite, 3 weight % ruthenium (based only on the graphite and ruthenium content) is shown in FIG. 4, which has a greatly magnified scale compared with FIGS. 1-3. As in FIGS. 1 and 2, "A" denotes a dry-to-wet step change in humidity, and "B" denotes a wet-to-dry change in humidity. The sharp peak at the start of the downward RH step is an experimental artefact due to a change in the flow conditions around the sensor during this test and is not related to the fundamental humidity behaviour.

The huge improvement in humidity transient performance obtained by the present invention is achieved without any significant reduction in the fundamental activity of the electrode towards NO.

However, it is invariably the case that improvements in some performance parameters may be accompanied by undesirable degradations in other aspects. In particular, a 3 weight % ruthenium loading is not optimum in terms of NO sensitivity and baseline signal, although both are within acceptable limits. Although, the temperature performance of the catalyst is not significantly modified by the presence of ruthenium. Ruthenium also increases the cross-sensitivity to sulphur-containing gases such as $H_2S$ and $SO_2$, but whilst undesirable, this is not a critical shortcoming because these contaminants are generally present only in very small amounts, or may be filtered out, for example using carbon cloth.

Thus a practical sensor design, capable of low level measurement of NO in exhaled breath employing the principle of RH interference cancellation is feasible.

Platinum also exhibits a positive response to relative humidity, and is therefore another potential candidate for achieving the required reduction or cancellation in the humidity response of a graphite gas sensing electrode. However, platinum may be less suitable than ruthenium as it is more sensitive to reaction with other gases that may be present in the environment, and which may also cause an interfering effect. Where, however, the sensor is not intended for use in such environments, this does not cause a problem.

Another metal which exhibits a negative humidity transient is gold. This can be reduced or cancelled out by mixing with an appropriate amount of another catalyst material having a positive humidity transient, such as ruthenium, ruthenium oxide or platinum.

Turning now to the remainder of the sensor components, the counter electrode may be any of the conventional types. In the case of a gas diffusion electrode, the counter electrode will typically be platinum black, for instance made by coating a platinum catalyst on to a porous hydrophobic support, typically in the form of a PTFE tape. Other forms of counter electrodes may be used depending on the sensor type, for instance metal foils, meshes or compressed powder tablets.

The electrolyte may take the form of a "free" liquid electrolyte, or the electrolyte may be immobilised, for instance in a separator of a conventional type, or the electrolyte may be in solid form. The nature of the electrolyte will depend upon the nature of the electrodes and the reactions to take place at those electrodes, and should be selected so as not to affect the humidity response of the sensor. In the context of a NO electrochemical gas sensor where the gas sensing electrode comprises a mixture of graphite and ruthenium, as described in detail above, the electrolyte will typically be protonic in nature. For example, the electrolyte may be a mineral acid, such as sulphuric acid, phosphoric acid, or any of the other acids conventionally used in electrochemical cell technology. Preferably, however, the electrolyte is sulphuric acid, more preferably with a molarity in the range 3 to 6 M, and most preferably with a molarity of about 5 M.

Generally, the sensor further comprises a housing. For ease of construction, the housing may comprise two parts, the first part providing the base of the sensor and the second part providing the top of the sensor. Alternatively, the housing could be made a single piece or in several pieces. A single piece design would, however, require that the electrodes are in situ before the moulding or forming process takes place, which can be difficult in practice.

The sensor may comprise electrodes in addition to the gas sensing electrode and the counter electrode. For instance, it may be desirable to include in the sensor a reference electrode with an external potentiostatic operating circuit. With this arrangement the gas sensing electrode is held at a fixed potential relative to the reference electrode, and as no current is drawn from the reference electrode both maintain a constant potential, which may be selected according to the nature of the reaction(s) taking place, or desired, at the sensing electrode.

The sensor may additionally or alternatively comprise an auxiliary electrode which will have essentially the same chemical composition as the gas sensing electrode, and which allows cancellation of current effects in the absence of the measurand, which may be highly temperature sensitive.

The gas sensing electrode may be fitted with a diffusion barrier to control the rate of gas supplied to the electrode. This may take any of the conventional forms, for instance it may be a porous membrane, a capillary barrier, a Knudsen barrier or solid membrane diffusion barrier, which relies on solid diffusion, as used for instance in $O_2$ sensors.

The present invention is now described in terms of the third aspect, and the additional considerations for use therein. In this aspect, the two gas sensing electrodes may be mounted on the same substrate or on different substrates. For instance, when they are mounted on the same substrate, the two electrodes may take the form of separate patches of first and second catalyst materials applied to the same porous PTFE tape. Other arrangements of different electrodes on the same support are known in the field, and apply to this embodiment of the present invention.

It is essential that the different gas sensing electrodes be exposed to the target gas and any interfering stimulus substantially at the same time, otherwise the effect of combining the responses from each of the electrodes may itself give rise to anomalies such that the ultimate sensor output does not accurately reflect the local concentration of the target gas. Techniques for achieving substantially simultaneous supply of the target gas to different gas sensing electrodes are known in the field, for instance as described in WO-A-2005015195.

It is necessary to provide an analysis circuit for each of the gas sensing electrodes. It may also be necessary to provide different bias circuits for the gas sensing electrodes, if it is desired that these should be held at different potential. Alternatively, selection of appropriate, different, reference electrodes may achieve the same effect without any biasing of the gas sensing electrodes.

Electronic processing techniques may be used to combine the responses of the different gas sensing electrodes to the interfering stimulus, and also their responses to the target gas if both are responsive thereto, so as to provide a sensor output that is related to the concentration of the target gas, by reducing or cancelling out the effect of the interfering stimulus. Conventional signal processing techniques can be used for this purpose, for instance the various responses of the sensing electrodes may be digitised and subsequently processed, or combined in analogue form.

The same counter electrode may be used for each of the gas sensing electrodes, provided that it has sufficient activity to support the reactions taking place in those gas sensing electrodes. Alternatively, a separate counter electrode may be used for each separate gas sensing electrode.

Returning now to the chemical make-up of the gas sensing electrodes, the considerations described above in relation to the first aspect of the present invention apply. However, additional considerations may need to be taken into account, for instance where the second catalyst material might have higher sensitivity to the interfering stimulus or to other cross-interferences when provided as a separate gas sensing electrode than when part of a catalyst mixture, due to its potentially higher concentration in this form.

By way of example, as is shown in FIG. 3, the optimum concentration of ruthenium in a graphite gas sensing electrode (in terms of cancelling out a humidity transient effect) is 3 weight % based upon the total weight of ruthenium and graphite present. When ruthenium is present at this low level its sensitivity to gaseous cross-interferents is very low. However, were ruthenium to be formulated as a 100 weight % ruthenium gas sensing electrode large currents would be generated in response to these cross-interferents, which would be highly undesirable. The effect of these gaseous cross-interferents may be removed through the use of a chemical filter, but a simpler solution to this potential problem is to reduce the concentration of ruthenium down to a level where sensitivity to other cross-interferents is minimal, for instance by mixing with a neutral (ie. with no electrochemical activity) support medium. This would also have the effect of reducing the response of the gas sensing electrode to the interfering stimulus.

Another way of reducing the response of a pure second catalyst material would be to use a reduced surface area as compared to the first catalyst material.

Another way of reducing the response of a pure second catalyst gas sensing electrode to a transient humidity effect would be to apply an appropriate correction factor to the signal generated so as to reduce this to a level which is substantially equal and opposite to the humidity transient response exhibited by the graphite gas sensing electrode. For instance, in the context of a ruthenium gas sensing electrode as ruthenium generates an opposite and substantially equal humidity transient effect to graphite at an amount of ruthenium of about 3 weight %, it would be appropriate to divide the signal generated by a pure (100 weight %) ruthenium electrode by a factor of about 30.

Yet another way of reducing the response of a pure second catalyst material would be to use a narrower capillary size for supplying the target gas to the electrode made from that second catalyst material.

While all the above considerations are possible, the gas sensor according to the first aspect of the present invention is preferred over that of the third aspect, due to its relative simplicity in a number of ways.

The present invention is now further described by way of the following Example.

Example

In the following, all references to % are to % by weight unless indicated to the contrary.

32.3 g of Type 4 Synthetic Graphite (available from Johnson Matthey), having a surface area of 5 to 20 m²/g and a median ($D_{50}$) particle size (by volume) in the range 15 to 25 µm and 1.00 g of Ruthenium Black (99.9% metals basis, available from Alfa Aesar, Germany), were milled together in a Turbula T2F mixing machine (available from Willy A. Bachofen AG) for 20 minutes at a mixing speed of 100 cycles/min., to form an homogeneous mixture of the two catalyst materials. The resulting catalyst mixture contained 97 weight % graphite and 3 weight % ruthenium black.

A liquid mixture was obtained by mixing together in a beaker 0.080 ml of 35% ammonia solution, 21 ml PTFE dispersion (60% PTFE, 6% Triton-X dispersant, 34% water) and 12 g of 1% polyacrylic acid solution. The catalyst mixture was added in small amounts to the liquid mixture and mixed until the powder was wetted and an homogeneous dispersion achieved. The resulting dispersion was then further mixed on a Silverson mixer, moving the beaker around the mixing head and slowly increasing the stirring speed up to 5500 revolutions per minute. Mixing was continued for a minimum of five minutes.

The resulting composition was then printed on to a porous PTFE backing tape (available from GORE) by stencil printing and cured, to a target deposition of 18 mg±2 mg dry weight.

The gas sensing electrode (2) was then built into a conventional stack assembly (1) as illustrated in FIG. 5. For clarity, the sensor housing and current collectors have been omitted from this Figure. The reference (3) and counter (4) electrodes were of a conventional platinum black construction, mounted on porous PTFE backing tapes allowing gas to permeate but preventing the passage of electrolyte out of the cell.

The electrolyte was 5M $H_2SO_4$. The separators (5) shown within the stack wet up the electrodes by drawing up electrolyte from a reservoir in the base of the sensor (not shown). The sensor was designed to operate with the sensing electrode biased at +350 mV relative to the reference electrode, and to be operated and controlled using a conventional potentiostatic circuit.

This particular sensor design incorporated an auxiliary electrode (6) whose purpose was to assist in the cancellation of background baseline effects which inevitably occur in electrochemical sensors. The auxiliary electrode had the same construction as the sensing electrode. Table 1, below, summarises the key performance parameters of the device. The cross-interferences were determined with a Zorflex® AC FM70 carbon cloth filter (available from Charcoal Cloth International) in place.

TABLE 1

| Parameter | Performance |
| --- | --- |
| Range | 0-2000 ppb (0-2 ppm) |
| Sensitivity | 1100-1500 nA/ppm |
| Response Time T90 | <30 seconds |
| Bias Voltage | +350 mV (±5 mV) |
| Drift | <2% signal year |
| Operating Temperature | 5-40° C. |
| Pressure | Atmospheric ±10% (mbar) |
| Sensor Life | >2 years |
| Cross Interferences: | |
| CO | <0.01% (<0.5 nA/ppm) |
| $H_2S$ | <0.8% (<10 nA/ppm) |
| $NO_2$ | <2.5% (<33 nA/ppm) |
| $H_2$ | <0.01% (<0.5 nA/ppm) |
| $SO_2$ | <0.01% (<0.5 nA/ppm) |

The invention claimed is:

1. An electrochemical gas sensor for sensing a target gas, the sensor comprising
   a gas sensing electrode;
   a counter electrode; and
   an electrolyte with which both the gas sensing electrode and the counter electrode are in contact,
   wherein the gas sensing electrode comprises a first catalyst material reactive to the target gas and which produces a response to an interfering stimulus, and a second catalyst material which produces a response to the interfering stimulus which is substantially equal in magnitude and of opposite polarity to the response of the first catalyst material to that interfering stimulus, and
   wherein the first and second catalyst materials are exposed to the target gas and any interfering stimulus at substantially the same time.

2. A sensor according to claim 1, wherein the interfering stimulus is humidity.

3. A sensor according to claim 1, wherein the first catalyst material is selected from graphite and gold, and the second catalyst material is selected from the transition metals and compounds thereof.

4. A sensor according to claim 3, wherein the first catalyst material is graphite.

5. A sensor according to claim 3, wherein the second catalyst material is ruthenium or platinum.

6. A sensor according to claim 4, wherein the second catalyst material is ruthenium or platinum.

7. A sensor according to claim 6, wherein the second catalyst material is ruthenium.

8. A sensor according to claim 4, wherein the second catalyst material is ruthenium and is present in an amount of greater than 0 weight % up to about 7 weight % of the total amount of ruthenium and graphite present in the gas sensing electrode.

9. A sensor according to claim 8, wherein the amount of ruthenium is in the range of about 2 weight % to about 4 weight % based upon the total weight of ruthenium and graphite present in the gas sensing electrode.

10. A sensor according to claim 9, wherein the amount of ruthenium is about 3 weight % based upon the total weight of ruthenium and graphite present in the gas sensing electrode.

11. A sensor according to claim 1, wherein the electrolyte is sulphuric acid.

12. A sensor according to claim 11, wherein the electrolyte is sulphuric acid having a molarity in the range of about 3 to 6 M.

13. An electrode for sensing a target gas in an electrochemical gas sensor, the electrode comprising, supported on or dispersed within a support material, a catalyst composition comprising a first catalyst material reactive to the target gas and which produces a response to an interfering stimulus, and a second catalyst material which produces a response to the interfering stimulus which is substantially equal to in magnitude and of opposite polarity to the response of the first catalyst material to the same interfering stimulus, wherein the first and second catalyst materials are exposed to the target gas and any interfering stimulus at substantially the same time.

14. An electrode according to claim 13, wherein the interfering stimulus is humidity.

15. An electrode according to claim 13, wherein the first catalyst material is selected from graphite and gold, and the second catalyst material is selected from the transition metals and compounds thereof.

16. An electrode according to claim 15, wherein the first catalyst material is graphite.

17. An electrode according to claim 15, wherein the second catalyst material is ruthenium or platinum.

18. An electrode according to claim 16, wherein the second catalyst material is ruthenium or platinum.

19. An electrode according to claim 18, wherein the second catalyst material is ruthenium.

20. An electrode according to claim 16, wherein the second catalyst material is ruthenium and the amount of ruthenium in the catalyst composition is in the range of greater than 0 weight % up to about 7 weight % based upon the total weight of graphite and ruthenium present in the catalyst composition.

21. An electrode according to claim 20, wherein the amount of ruthenium in the catalyst composition is in the range of about 2 weight % to about 4 weight % of the total amount of ruthenium and graphite in the catalyst composition.

22. An electrode according to claim 21 wherein the amount of ruthenium in the catalyst composition is about 3 weight % of the total amount of ruthenium and graphite in the catalyst composition.

23. An electrochemical gas sensor for sensing a target gas comprising an electrochemical gas sensor for sensing a target gas and generating a sensor output related to the concentration of the target gas, the sensor comprising a first gas sensing electrode comprising a first catalyst material reactive to the target gas and which produces a response to an interfering stimulus;

a second gas sensing electrode comprising a second catalyst material which produces a response to the interfering stimulus which is substantially equal in magnitude and of opposite polarity to the response of the first catalyst material to that interfering stimulus;

a counter electrode; and an electrolyte with which each of the gas sensing electrodes and the counter electrode are in contact;

and circuitry for electronically processing the responses of the first and second gas sensing electrodes, so as to reduce or cancel out the effect on sensor output of the interfering stimulus, wherein the first and second catalyst materials are exposed to the target gas and any interfering stimulus at substantially the same time.

24. A sensor according to claim 23, wherein the first catalyst material is selected from graphite and gold, and the second catalyst material is selected from the transition metals and compounds thereof.

25. A sensor according to claim 24, wherein the first catalyst material is graphite.

26. A sensor according to claim 24, wherein the second catalyst material is selected from ruthenium and platinum.

27. A sensor according to claim 25, wherein the second catalyst material is selected from ruthenium or platinum.

28. A sensor according to claim 27, wherein the second catalyst material ruthenium.

* * * * *